United States Patent
Wagner et al.

(10) Patent No.: US 12,378,169 B2
(45) Date of Patent: *Aug. 5, 2025

(54) PROCESS FOR OBTAINING ISOBUTENE FROM A C4-HYDROCARBON MIXTURE

(71) Applicant: BASF SE, Ludwigshafen am Rhein (DE)

(72) Inventors: Hans-Guenter Wagner, Ludwigshafen am Rhein (DE); Randolph Hugo, Ludwigshafen am Rhein (DE); Thomas Roussiere, Ludwigshafen am Rhein (DE); Suman Thotla, Ludwigshafen am Rhein (DE); Gerrit Waters, Ludwigshafen am Rhein (DE); Michael Huebner, Freeport, TX (US); Markus Neudert, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 48 days.

This patent is subject to a terminal disclaimer.

(21) Appl. No.: 18/280,689

(22) PCT Filed: Mar. 1, 2022

(86) PCT No.: PCT/EP2022/055186
§ 371 (c)(1),
(2) Date: Sep. 7, 2023

(87) PCT Pub. No.: WO2022/189218
PCT Pub. Date: Sep. 15, 2022

(65) Prior Publication Data
US 2024/0140885 A1    May 2, 2024

(30) Foreign Application Priority Data
Mar. 8, 2021  (EP) .................................... 21161227

(51) Int. Cl.
*C07C 5/32* (2006.01)
*C07C 7/00* (2006.01)
(Continued)

(52) U.S. Cl.
CPC .............. *C07C 5/321* (2013.01); *C07C 7/005* (2013.01); *C07C 7/04* (2013.01); *C07C 7/14891* (2013.01)

(58) Field of Classification Search
CPC ........... C07C 5/321; C07C 7/005; C07C 7/04; C07C 7/14891; C07C 1/20; C07C 29/10;
(Continued)

(56) References Cited

U.S. PATENT DOCUMENTS

| | | | |
|---|---|---|---|
| 4,287,379 A | 9/1981 | Brunner et al. | |
| 4,320,232 A | 3/1982 | Volkamer et al. | |

FOREIGN PATENT DOCUMENTS

| | | |
|---|---|---|
| CN | 1158228 C | 7/2004 |
| CN | 1239444 C | 2/2006 |

(Continued)

OTHER PUBLICATIONS

International Search Report and Written Opinion received for PCT Patent Application No. PCT/EP2022/055186, mailed on Jun. 7, 2022, 8 pages.

*Primary Examiner* — Thuan D Dang
(74) *Attorney, Agent, or Firm* — Faegre Drinker Biddle & Reath LLP

(57) ABSTRACT

The invention relates to a process for obtaining isobutene from an isobutene containing C4-hydrocarbon mixture (1) in a plant comprising an etherification unit (3), a first distillation unit (5), an ether cleavage unit (8) and a second distillation unit (10), the process comprising: (a) contacting the C4-hydrocarbon mixture (1) with a primary alcohol (2)

(Continued)

and reacting the mixture with the primary alcohol in the presence of an acidic catalyst to form the corresponding alkyl tert-butyl ether as an intermediate product and diisobutene as a by-product in the etherification unit (3); (b) distilling the reaction mixture (4) from the etherification unit (3) in the first distillation unit (5), a C4-hydrocarbon raffinate being withdrawn as the overhead product (6), the alkyl tert-butyl ether and diisobutene being withdrawn as the liquid or vaporous bottom product (7), and vaporizing the bottom product (7) if it is withdrawn as a liquid; (c) reacting the vaporous bottom product (7) in the presence of an acidic catalyst obtaining isobutene and the primary alcohol as reaction products in the ether cleavage unit (8); (d) distilling the reaction mixture (9) from the ether cleavage unit (8) in the second distillation unit (10), isobutene being withdrawn as the overhead product (11), the primary alcohol and diisobutene being withdrawn as the bottom product (12) and being recycled to the etherification unit (3); the plant further comprising a byproduct separation unit (15) being fed by a bottom purge stream (13) of the first distillation unit (5) and/or by a part of the bottom product of the second distillation unit (10), this feed stream (14) being split up in at least three byproduct streams wherein a first byproduct stream (16) is rich in diisobutene, a second byproduct stream (17) is rich in the primary alcohol, and a third byproduct stream (18) is rich in components with a normal boiling point higher than 110° C.

12 Claims, 2 Drawing Sheets

(51) Int. Cl.
*C07C 7/04* (2006.01)
*C07C 7/148* (2006.01)

(58) Field of Classification Search
CPC ......... C07C 29/80; C07C 41/06; C07C 41/58; C07C 11/09; C07C 41/42; C07C 43/046; B01D 3/143
See application file for complete search history.

(56) References Cited

FOREIGN PATENT DOCUMENTS

| | | |
|---|---|---|
| EP | 0003305 A2 | 8/1979 |
| EP | 0022509 A1 | 1/1981 |

US 12,378,169 B2

PROCESS FOR OBTAINING ISOBUTENE FROM A C4-HYDROCARBON MIXTURE

CROSS-REFERENCE TO RELATED APPLICATIONS

This application is a National stage application (under 35 U.S.C. § 371) of PCT/EP2022/055186, filed Mar. 1, 2022, which claims benefit of European Application No. 21161227.0, filed Mar. 8, 2021, both of which are incorporated herein by reference in their entirety.

The invention relates to a process for obtaining isobutene from an isobutene containing C4-hydrocarbon mixture in a plant comprising an etherification unit, a first distillation unit, an ether cleavage unit and a second distillation unit.

C4 fractions from steam crackers or fluid catalytic cracker (FCC) units consist essentially of butadiene, isobutene, 1-butene and 2-butenes together with the saturated hydrocarbons isobutane and n-butane. Customary work-up methods used worldwide for such C4 fractions include the following steps: first, the major part of the butadiene is removed. A hydrocarbon mixture referred to as Raffinate 1, that includes the saturated hydrocarbons together with isobutene, 1-butene and 2-butenes remains. A possible way of removing the isobutene from this mixture is reaction with a primary alcohol to form an alkyl tert-butyl ether. This leaves the saturated hydrocarbons and linear butenes. The C4 mixture obtained after removal of the butadiene and isobutene is referred to as Raffinate 2.

The document EP 0003305 A2 discloses a process for removing isobutene from a isobutene containing C4-hydrocarbon mixture, which comprises (a) reacting the mixture with a primary alcohol in the presence of an acidic ion exchange resin to form an alkyl tert-butyl ether; (b) distilling the reaction mixture to obtain an overhead product comprising the unconverted hydrocarbons, and a bottom product comprising the alkyl tert-butyl ether; (c) feeding the bottom product to an ether cleavage unit to decompose the alkyl tert-butyl ether to obtain isobutene and primary alcohol; (d) distilling the mixture of isobutene and primary alcohol produced in step (c) to obtain an overhead product comprising isobutene, and a bottom product comprising the primary alcohol; and (e) recycling the bottom product of step (d) to step (a).

The document CN 1158228 C discloses a process for manufacturing isoolefins and/or tertiary alkyl ethers by reacting a mixed hydrocarbon stream containing the isoolefin with an alcohol, obtaining a tertiary alkyl ether product. The tertiary alkyl ether product is separated in a distillation column where a highly pure tertiary alkyl ether product is withdrawn as side draw from the stripping section of the distillation column so as to reduce equipment costs and energy consumption for preparing tertiary alkyl ethers and/or isoolefins.

The document CN 1239444 C discloses a process for the production of isoolefins, which comprises (a) feeding an isoolefin-containing hydrocarbon mixture and alcohols into an etherification reactor, (b) separating an obtained product that mainly contains tertiary alkyl ether in a first fractionator and a second fractionator, (c) heating the product by a heater and then feeding it into an ether cracking reactor to obtain a product mainly containing unreacted tertiary alkyl ether, isoolefins, and alcohols, and (d) subjecting the product to high-boiling fraction removal by a third fractionator to obtain isoolefins.

Even though there are installations of plants for reactive separation of isobutene from a C4-hydrocarbon mixture, there remain some challenges in operating these plants with respect to their operational window, i.e. the range of process conditions that should be fulfilled in order to guarantee a stable operation of the plant. Typically, these plants are designed for a predetermined range of feed components. As soon as a larger deviation in components or their mass fractions occurs, it becomes difficult or even impossible to operate the plant in a stable mode. A further challenge is that the plants are designed to work in closed loops concerning the formation of alkyl tert-butyl ether and its back-splitting to isobutene and alcohol and recycling the alcohol to the ether formation reactor. Initially small disturbances in this loop like impurities may build up and lead to situations that necessitate a temporary shut-down of the plant or parts of the plant.

It was an object of the invention to provide a process for the reactive separation of isobutene from a C4-hydrocarbon mixture via forming and back-splitting of an alkyl tert-butyl ether that is more robust to internal or external disturbances.

This object is achieved according to the invention by a process according to claim 1. Advantageous variants of the process are presented in claims 2 to 12.

Subject of the invention is a process for obtaining isobutene from an isobutene containing C4-hydrocarbon mixture in a plant comprising an etherification unit, a first distillation unit, an ether cleavage unit and a second distillation unit, the process comprising:
  (a) contacting the C4-hydrocarbon mixture with a primary alcohol and reacting the mixture with the primary alcohol in the presence of an acidic catalyst to form the corresponding alkyl tert-butyl ether as an intermediate product and diisobutene as a by-product in the etherification unit;
  (b) distilling the reaction mixture from the etherification unit in the first distillation unit, a C4-hydrocarbon raffinate being withdrawn as the overhead product, the alkyl tert-butyl ether and diisobutene being withdrawn as the liquid or vaporous bottom product, and vaporizing the bottom product if it is withdrawn as a liquid;
  (c) reacting the vaporous bottom product in the presence of an acidic catalyst obtaining isobutene and the primary alcohol as reaction products in the ether cleavage unit; and
  (d) distilling the reaction mixture from the ether cleavage unit in the second distillation unit, isobutene being withdrawn as the overhead product, the primary alcohol and diisobutene being withdrawn as the bottom product and being recycled to the etherification unit.

According to the invention the plant further comprises a byproduct separation unit being fed by a bottom purge stream of the first distillation unit and/or by a part of the bottom product of the second distillation unit, this feed stream being split up in at least three byproduct streams wherein a first byproduct stream is rich in diisobutene, a second byproduct stream is rich in the primary alcohol, and a third byproduct stream is rich in components with a normal boiling point higher than 110° C.

The provision of a byproduct separation unit that is fed by a bottom purge stream of the first distillation unit and/or by a part of the bottom product of the second distillation unit significantly increases the operational window of a plant for obtaining isobutene from an isobutene containing C4-hydrocarbon mixture. The removal of a bottom purge stream of the first distillation unit and/or of a part of the bottom product of the second distillation unit enables the continuous removal of high boiling impurities from the system. The removal of high boiling components from the system can be accomplished in different ways. In a preferred embodiment the byproduct separation unit is fed by a bottom purge stream of the first distillation unit. In another preferred embodiment the byproduct separation unit is fed by a part of the bottom product of the second distillation unit. In another preferred embodiment the byproduct separation unit is fed by a bottom purge stream of the first distillation unit and by a part of the bottom product of the second distillation unit.

The process according to the invention is more robust against internal disturbances like build-up of impurities as well as external disturbances like variations in feed composition. Furthermore, the separation of the withdrawn part of the bottom product of the second distillation unit into three different fractions enables a more specific recycling strategy, a higher process integration and thus reduction of operating costs. The valuable by-product diisobutene is easily recovered in contrast to known processes where it is discharged.

Isobutene-containing C4-hydrocarbon mixtures suitable for the process of the invention are obtained, for example, from the thermal or catalytic cracking of petroleum products, from the pyrolysis of liquefied petroleum gas (LPG), naphtha, gas oil or the like, or from the catalytic dehydrogenation of n-butane and/or n-butene. In general, these C4-hydrocarbon mixtures contain olefinic and paraffinic C4-hydrocarbons in addition to the isobutene. They may also contain butadiene and acetylenes, e.g., 1-butyne and butenyne. Butadiene-containing C4-hydrocarbon mixtures may be employed as such or after removal of the butadiene from the C4-hydrocarbon mixture, for example by extraction with a selective solvent. In general, the isobutene-containing C4-hydrocarbon mixture contains from 5 to 95% by weight, preferably from 10 to 90% by weight, in particular from 20 to 70% by weight, of isobutene. Preferably, C4-hydrocarbon mixtures are used which in addition to isobutene contain n-butane, isobutane, 1-butene, trans-2-butene and cis-2-butene, with or without 1,3-butadiene. More preferably, a C4-hydrocarbon mixture without 1,3-butadiene, known as "Raffinate-1", is used for the process of the invention.

Primary alcohols suitable for the process of the invention are those that can react with isobutene to form the corresponding alkyl tert-butyl ether. Preferably, the primary alcohol is selected from the group of methanol, ethanol, isopropyl alcohol and isobutanol. More preferably, the primary alcohol is isobutanol.

In a first embodiment of the subject of the invention, the primary alcohol is methanol and the alkyl tert-butyl ether is methyl tert-butyl ether (MTBE). The process for obtaining isobutene from an isobutene containing C4-hydrocarbon mixture in a plant comprising an etherification unit, a first distillation unit, an ether cleavage unit and a second distillation unit, comprises the following steps:

(a) contacting the C4-hydrocarbon mixture with methanol and reacting the mixture with methanol in the presence of an acidic catalyst to form methyl tert-butyl ether (MTBE) as an intermediate product and diisobutene as a by-product in the etherification unit;

(b) distilling the reaction mixture from the etherification unit in the first distillation unit, a C4-hydrocarbon raffinate being withdrawn as the overhead product, MTBE and diisobutene being withdrawn as the liquid or vaporous bottom product, and vaporizing the bottom product if it is withdrawn as a liquid;

(c) reacting the vaporous bottom product in the presence of an acidic catalyst obtaining isobutene and methanol as reaction products in the ether cleavage unit; and (d) distilling the reaction mixture from the ether cleavage unit in the second distillation unit, isobutene being withdrawn as the overhead product, methanol and diisobutene being withdrawn as the bottom product and being recycled to the etherification unit;

wherein the plant further comprises a byproduct separation unit being fed by a bottom purge stream of the first distillation unit and/or by a part of the bottom product of the second distillation unit, this feed stream being split up in at least three byproduct streams wherein a first byproduct stream is rich in diisobutene, a second byproduct stream is rich in methanol, and a third byproduct stream is rich in components with a normal boiling point higher than 110° C.

In a second embodiment of the subject of the invention, the primary alcohol is ethanol and the alkyl tert-butyl ether is ethyl tert-butyl ether (ETBE). The process for obtaining isobutene from an isobutene containing C4-hydrocarbon mixture in a plant comprising an etherification unit, a first distillation unit, an ether cleavage unit and a second distillation unit, comprises the following steps:

(a) contacting the C4-hydrocarbon mixture with ethanol and reacting the mixture with ethanol in the presence of an acidic catalyst to form ethyl tert-butyl ether (ETBE) as an intermediate product and diisobutene as a by-product in the etherification unit;

(b) distilling the reaction mixture from the etherification unit in the first distillation unit, a C4-hydrocarbon raffinate being withdrawn as the overhead product, ETBE and diisobutene being withdrawn as the liquid or vaporous bottom product, and vaporizing the bottom product if it is withdrawn as a liquid;

(c) reacting the vaporous bottom product in the presence of an acidic catalyst obtaining isobutene and ethanol as reaction products in the ether cleavage unit; and (d) distilling the reaction mixture from the ether cleavage unit in the second distillation unit, isobutene being withdrawn as the overhead product, ethanol and diisobutene being withdrawn as the bottom product and being recycled to the etherification unit;

wherein the plant further comprises a byproduct separation unit being fed by a bottom purge stream of the first distillation unit and/or by a part of the bottom product of the second distillation unit, this feed stream being split up in at least three byproduct streams wherein a first byproduct stream is rich in diisobutene, a second byproduct stream is rich in ethanol, and a third byproduct stream is rich in components with a normal boiling point higher than 110° C.

In a third embodiment of the subject of the invention, the primary alcohol is isopropyl alcohol and the alkyl tert-butyl ether is isopropyl tert-butyl ether (IPTBE). The process for obtaining isobutene from an isobutene containing C4-hydrocarbon mixture in a plant comprising an etherification unit, a first distillation unit, an ether cleavage unit and a second distillation unit, comprises the following steps:

(a) contacting the C4-hydrocarbon mixture with isopropyl alcohol and reacting the mixture with isopropyl alcohol in the presence of an acidic catalyst to form isopropyl tert-butyl ether (IPTBE) as an intermediate product and diisobutene as a by-product in the etherification unit;

(b) distilling the reaction mixture from the etherification unit in the first distillation unit, a C4-hydrocarbon raffinate being withdrawn as the overhead product, IPTBE and diisobutene being withdrawn as the liquid or vaporous bottom product, and vaporizing the bottom product if it is withdrawn as a liquid;

(c) reacting the vaporous bottom product in the presence of an acidic catalyst obtaining isobutene and isopropyl alcohol as reaction products in the ether cleavage unit; and (d) distilling the reaction mixture from the ether cleavage unit in the second distillation unit, isobutene being withdrawn as the overhead product, isopropyl alcohol and diisobutene being withdrawn as the bottom product and being recycled to the etherification unit;

wherein the plant further comprises a byproduct separation unit being fed by a bottom purge stream of the first distillation unit and/or by a part of the bottom product of the second distillation unit, this feed stream being split up in at least three byproduct streams wherein a first byproduct stream is rich in diisobutene, a second byproduct stream is rich in isopropyl alcohol, and a third byproduct stream is rich in components with a normal boiling point higher than 110° C.

In a fourth embodiment of the subject of the invention, the primary alcohol is isobutanol and the alkyl tert-butyl ether is isobutyl tert-butyl ether (IBTBE). The process for obtaining isobutene from an isobutene containing C4-hydrocarbon mixture in a plant comprising an etherification unit, a first distillation unit, an ether cleavage unit and a second distillation unit, comprises the following steps:

(a) contacting the C4-hydrocarbon mixture with isobutanol and reacting the mixture with isobutanol in the presence of an acidic catalyst to form isobutyl tert-butyl ether (IBTBE) as an intermediate product and diisobutene as a by-product in the etherification unit;

(b) distilling the reaction mixture from the etherification unit in the first distillation unit, a C4-hydrocarbon raffinate being withdrawn as the overhead product, IBTBE and diisobutene being withdrawn as the liquid or vaporous bottom product, and vaporizing the bottom product if it is withdrawn as a liquid;

(c) reacting the vaporous bottom product in the presence of an acidic catalyst obtaining isobutene and isobutanol as reaction products in the ether cleavage unit; and (d) distilling the reaction mixture from the ether cleavage unit in the second distillation unit, isobutene being withdrawn as the overhead product, isobutanol and diisobutene being withdrawn as the bottom product and being recycled to the etherification unit;

wherein the plant further comprises a byproduct separation unit being fed by a bottom purge stream of the first distillation unit and/or by a part of the bottom product of the second distillation unit, this feed stream being split up in at least three byproduct streams wherein a first byproduct stream is rich in diisobutene, a second byproduct stream is rich in isobutanol, and a third byproduct stream is rich in components with a normal boiling point higher than 110° C., preferably higher than 120° C.

Etherification Unit

The etherification is based on the selective reaction of the primary alcohol with isobutene contained in the isobutene-containing C4-hydrocarbon mixture, such as Raffinate 1. The product formed is the respective alkyl tert-butyl ether. Other C4-hydrocarbons do not participate in the etherification reaction. The etherification may be carried out in, for example, one or more stirred kettles or one or more fixed bed reactors, the latter being preferred.

Diisobutene is formed as the main by-product during the etherification reaction. Tertiary butanol may be formed as a further by-product, especially if water and isobutene are present on an acidic catalyst.

The etherification reaction occurs in the presence of an acidic ion-exchange resin, which acts as a heterogeneous etherification catalyst. The acidic ion-exchange resin is a cation exchanger in the acid form. In one embodiment, the acidic ion-exchange resin comprises a sulfonic or phosphoric ion-exchange resin. Preferably, the acidic, ion-exchange resin comprises a macro-reticular ion-exchange resin. Examples of suitable ion exchange resins are sulfonated phenol-formaldehyde resins, sulfonated resins derived from coumarone-indene condensation products and, in particular, sulfonated polystyrene resins. In a preferred embodiment, the acidic ion-exchange resin comprises a copolymer of styrene and divinylbenzene, e.g. a cross-linked styrene-divinylbenzene copolymer, functionalized with sulfonic acid groups.

In an embodiment, the acidic, ion-exchange resin can have a concentration of acidic ion-exchange groups of at least about 1 milliequivalent H+ per gram dry resin. In general, the amount of the ion exchange resin is from 0.01 to 1 liter of bulk volume per liter of reactor volume.

The etherification reaction is an equilibrium reaction. Thus, to reach equilibrium, a certain residence time is required. However, from a practical point of view, it is preferred to carry out the etherification continuously, in which case the quotient of the volume of the reaction zone (in volume units) and the throughput in volume units per hour is in general from 0.01 to 5 hours, preferably from 0.02 to 1 hour, especially from 0.03 to 1 hour.

In general, the etherification reaction results in not less than 90%, preferably not less than 95%, in particular not less than 96%, conversion of the isobutene, contained in the C4-hydrocarbon mixture, to the alkyl tert-butyl ether.

A molar excess of the primary alcohol in respect to isobutene is advantageous to reach a high conversion of isobutene and to suppress the formation of isobutene oligomers. The conversion increases with increasing molar ratio of the primary alcohol to isobutene. Preferably, the molar ratio of the primary alcohol to the isobutene contained in the C4-hydrocarbon mixture is from 100:1 to 1:1, more preferably from 20:1 to 1.2:1, especially from 4:1 to 1.3:1.

The etherification can be carried out under atmospheric pressure. However, it is advantageous to work under excess pressure, for example at from 1.01 to 30 bar, especially from 2 to 20 bar. The isobutene-containing C4-hydrocarbon mixture can, depending on the pressure and temperature, be employed as a liquid or a gas. Preferably, liquid isobutene-containing C4-hydrocarbon mixtures are employed. The pressure will be kept in the range of 12 to 20 bar to ensure that no vaporization occurs within the etherification unit.

Preferably, the exit temperature of the reaction mixture from the etherification unit is from 25 to 65° C., preferably from 30 to 60° C., especially from 30 to 50° C. The etherification is an exothermic reaction. The ether formation is favored at low temperatures. In order to reach high reaction rates and high isobutene conversion along with low byproduct formation, the reactor system is preferably cascaded and temperatures below 70° C. are applied. In an embodiment, a plurality of adiabatic fixed bed reactors is used in series, e.g., three adiabatic fixed bed reactors. The typical reactor inlet temperature is in the range of 30 to 40° C. The conversion is highest in the first reactor, the second reactor converts the remaining isobutene and the last reactor has a larger residence time to achieve the equilibrium condition of the etherification reaction.

With increasing age of the catalyst, the main contribution to the total conversion shifts from first to second reactor. The inlet temperature of the reactors is adjusted to achieve the intended conversion and depends on the activity of each of the catalysts. The inlet temperature of the third reactor will normally be the lowest and is kept as low as possible while still achieving equilibrium conditions at the outlet of this reactor.

In general, the catalyst of the first reactor will be replaced more frequently than the catalyst of the second and the third reactor as contaminants within the feedstock will deactivate the catalyst of the first reactor with a higher probability and conversion is typically highest within the first reactor.

The provision of parallel reactors in a reactor stage allows for an exchange of catalyst without the need to shut down the whole etherification unit. Reactors connected in parallel can be provided in any reactor stage, e.g. two first reactors, two second reactors and/or two third reactors.

First Distillation Unit

The reaction mixture withdrawn from the etherification unit contains alkyl tert-butyl ether, diisobutene, unconverted hydrocarbons and unreacted primary alcohol. The C4-hydrocarbons, which have not participated in the etherification reaction are separated from the alkyl tert-butyl ether and the excess primary alcohol in a first distillation unit. The top product taken off is a C4-hydrocarbon raffinate substantially free from isobutene. In general, the isobutene content is 5% by weight or less, preferably 2.5% by weight or less, especially 1.5% by weight or less. The isobutene content within the top product is determined by the conversion in the etherification unit and the initial composition of the isobutene-containing C4-hydrocarbon mixture, e.g., Raffinate 1. The isobutene content within the top product can be reduced by recycling part of the top product to the etherification unit.

Preferably, the combined amount of alkyl tert-butyl ether and/or di-isobutyl ether in the top product is not more than 200 ppm by weight. The top product is also named "Raffinate 2".

Preferably, the Raffinate 2 product stream is withdrawn in a side draw at the top of the distillation column. Components with a lower boiling point than that of the Raffinate 2 components are preferably withdrawn from a top condenser of the distillation column as off-gas. Those lighter components may comprise nitrogen, C3 hydrocarbons or potentially formed tertiary butanol.

The bottom product from the first distillation unit comprises mainly alkyl tert-butyl ether and diisobutene as well as components with a higher boiling point than the alkyl tert-butyl ether. The bottom product may or may not contain excess primary alcohol. Advantageously, a bottom product containing not more than 1,000 ppm by weight, preferably not more than 500 ppm by weight, especially not more than 100 ppm by weight, of C4-hydrocarbons is taken off.

Conveniently, the first distillation unit is operated under a pressure of about 4 to 8 bar and the bottom temperature is 165 to 200° C., for example about 170° C.

In one embodiment of the process according to the invention the alkyl tert-butyl ether containing bottom product from the first distillation unit is withdrawn in the vapor phase, for example as a vapor side draw from a distillation column.

In another embodiment the alkyl tert-butyl ether containing bottom product from the first distillation unit is withdrawn in the liquid phase. In this case, the bottom product is vaporized. Possible vaporizers are all customary types of vaporizer, e.g. falling film evaporators, helical tubes, thin film evaporators, natural convection evaporators with external or internal circulation, for example a Robert evaporator, or forced circulation evaporators. Preference is given to a Robert evaporator or a falling film evaporator.

It is further preferred that the vapor phase is superheated in order to prevent condensation on the ether cleavage catalyst due to endothermic reaction and pore condensation.

In a first preferred embodiment the first distillation unit comprises a distillation column, the bottom product being withdrawn as a side stream from the distillation column at a stage below the feed stage, and a bottom purge stream rich in high-boiling components being withdrawn from the sump of the distillation column. The side stream may be withdrawn as a vapor or as a liquid. Withdrawing the bottom product as a side stream has the advantage that high-boiling components that may lead to deterioration of the ether cleavage process are drastically reduced in the bottom product.

It is further preferred for this embodiment that the bottom purge stream from the sump of the distillation column in the first distillation unit is fed to the byproduct separation unit. The bottom purge stream containing the high-boiling components can be separated into valuable products in the byproduct separation unit. This increases the overall efficiency of the isobutene separation process by reducing the loss of byproducts.

In a second preferred embodiment the bottom product from the first distillation unit is vaporized in an evaporator, a bottom purge stream containing high boiling components with a normal boiling point higher than that of the alkyl tert-butyl ether being withdrawn from the evaporator.

Removing high boiling components in the evaporator before the ether cleavage unit has the advantage that a potential accumulation of those high boiling components in the closed process is prevented, which leads to an increase of capacity of the isobutene separation process. Furthermore, a potential catalyst deactivation in the ether cleavage unit is prevented.

It is further preferred for this embodiment that the evaporator is a natural circulation evaporator, particularly a Robert type evaporator, and that the bottom purge stream is withdrawn from the liquid phase in the bottom of the evaporator. Thereby, the high boiling components can be removed in an easy and efficient way.

It is further preferred for this embodiment that the bottom purge stream from the evaporator is fed to the byproduct separation unit. The bottom purge stream containing the high-boiling components can be separated into valuable products in the byproduct separation unit. This increases the overall efficiency of the isobutene separation process by reducing the loss of byproducts.

Ether Cleavage Unit

In the ether cleavage unit, the alkyl tert-butyl ether is decomposed into isobutene and the primary alcohol in the presence of an acid catalyst at elevated temperatures. Preferably, the alkyl tert-butyl ether containing bottom product from the first distillation unit is transferred to the ether cleavage unit without removal of any excess primary alcohol which may be present. Alternatively, it is possible to remove part or all of the primary alcohol.

The decomposition of the alkyl tert-butyl ether is performed in the vapor phase on the acid catalyst. It may be carried out batchwise but is preferably carried out continuously.

The ether cleavage reaction is an equilibrium reaction and the splitting is favored by high temperatures. The typical conversion is greater than 90%. The ether cleavage reaction may be carried out in one or more reactors connected in series and/or in parallel. Useful reactors include heated tubular reactors, such as steam-heated tubular reactors, or two reactor systems consisting of a heated tubular reactor followed by a second heated tubular reactor or an adiabatic fixed bed reactor. As an alternative, the ether cleavage reaction can be performed in a two-phase system using two-phase reactors.

Examples of suitable acid catalysts are ion exchangers in the acid form, e.g., sulfonated coal, sulfonated phenol-formaldehyde resins, sulfonated resins derived from coumarone-indene condensation products and, in particular, sulfonated polystyrene resins, e.g., sulfonated, crosslinked styrene-divinylbenzene copolymers.

Other catalysts which may be used advantageously are solid phosphoric acid catalysts which comprise monophosphoric acid or preferably polyphosphoric acid on a solid carrier. Examples of suitable carriers for the phosphoric acid catalysts are alumina, silica, active charcoal, kieselguhr or pumice. Silica gel is the preferred carrier.

Other suitable acid catalysts are metal sulfates, e.g., sodium bisulfate, calcium bisulfate, aluminum sulfates, nickel sulfate, copper sulfate, cobalt sulfate, cadmium sulfate and strontium sulfate. These sulfates may be used unsupported but are preferably used on a carrier. Examples of suitable carriers are silica gel, active charcoal, alumina and pumice.

Further suitable catalysts for the decomposition are silica gel or alumina as such.

In a further embodiment of the process according to the invention, a metal phosphate, especially a metal hydrogen phosphate, is used as the acid decomposition catalyst. These phosphates may also contain phosphoric acid in excess over the amount corresponding to the stoichiometric composition of the acid metal phosphate, for example in an excess of up to 65%, preferably from 1 to 50%, in particular from 10 to 20%. Examples of such metal phosphates are magnesium phosphates, calcium phosphates, strontium phosphates, barium phosphates, manganese phosphates, nickel phosphates, copper phosphates, cobalt phosphates, cadmium phosphates, iron (II) phosphates, chromium phosphates and in particular aluminum phosphates.

The metal phosphate catalyst can be used as such or on a carrier. Examples of suitable carriers are alumina, silica, active charcoal and zinc oxide.

The amount of the acid catalyst is in general from about 0.01 to 1 kg, preferably from about 0.03 to 0.3 kg, per kg of alkyl tert-butyl ether passed through the reactor per hour. Preferably, fixed bed reactors are used for the decomposition of the alkyl tert-butyl ether.

The decomposition temperature of the tertiary ether varies with the nature of the acid catalyst and with the contact time, but is in general from 50° C. to 350° C., preferably from 80° C. to 300° C., in particular from 100° C. to 250° C. If a metal phosphate or phosphoric acid catalyst is used as the decomposition catalyst, the decomposition is in general carried out at from 80° C. to 350° C., preferably from 90° C. to 260° C., especially from 170° C. to 210° C.

The contact time of the vaporized alkyl tert-butyl ether is advantageously from 0.1 to 20 seconds, preferably from 1 to 10 seconds.

The decomposition of the alkyl tert-butyl ether can be carried out under atmospheric pressure, but is in general carried out under excess pressure, for example at up to 30 bar, preferably up to 20 bar. Advantageously, the decomposition of the alkyl tert-butyl ether is carried out under pressures of from 2 to 15 bar, preferably from 3 to 12 bar, especially from 4 to 12 bar. However, the decomposition can also be carried out under reduced pressure.

In an embodiment, the ether cleavage unit comprises a first ether cleavage reactor and a second ether cleavage reactor connected in series. Due to high initial activity of the first ether cleavage reactor nearly full conversion is reached in this reactor. The absence of cleavable ether in the output of the first reactor may give rise to undesired side reactions in the second reactor, such as dehydration of the primary alcohol to water and isobutene. When the activity of the first ether cleavage reactor lowers over time and the output of the first ether cleavage reactor contains a predetermined concentration of alkyl tert-butyl ether, the second ether cleavage reactor is taken into operation.

In preferred embodiments, the first ether cleavage reactor and the second ether cleavage reactor are periodically caused to alternate in sequence and/or flow direction through the first ether cleavage reactor and/or the second ether cleavage reactor is periodically changed. The possibility to switch between the two reactors and to periodically change flow direction through reactors may lead to more uniform deactivation over the reactor length and better reaction control. Ultimately, overall runtime can be improved.

Second Distillation Unit

The reaction mixture obtained from the ether cleavage unit, which contains isobutene and primary alcohol as reaction products, is fed to a second distillation unit. In the second distillation unit, high purity isobutene is separated from heavier components such as primary alcohol, non-reacted alkyl tert-butyl ether, and further heavier compounds, e.g. diisobutene, by distillation.

In the first embodiment of the subject of the invention, where the primary alcohol is methanol and the alkyl tert-butyl ether is methyl tert-butyl ether (MTBE), the second distillation unit preferably comprises a methanol extraction unit and an isobutene purification column. The reaction mixture from the ether cleavage unit is fed to the methanol extraction unit where it is counter-currently contacted with a solvent, preferably with water as a solvent. A stream rich in water and methanol is withdrawn from the bottom of the extraction unit for further processing and recycling methanol to the etherification unit. A stream rich in isobutene is withdrawn from the top of the extraction unit and is fed to the isobutene purification column where isobutene is separated from higher boiling components and is withdrawn as the overhead product of the isobutene purification column. Preferably, the isobutene product stream is withdrawn in a side draw at the top of the isobutene purification column while the column is operated at total liquid reflux. Components with a lower boiling point than that of isobutene are preferably withdrawn from a top condenser of the column as off-gas. Those lighter components may comprise nitrogen or C3 hydrocarbons.

In the second embodiment of the subject of the invention, where the primary alcohol is ethanol and the alkyl tert-butyl ether is ethyl tert-butyl ether (ETBE), the second distillation unit preferably comprises an ethanol extraction unit and an isobutene purification column. The reaction mixture from the ether cleavage unit is fed to the ethanol extraction unit where it is counter-currently contacted with a solvent, preferably with water as a solvent. A stream rich in water and ethanol is withdrawn from the bottom of the extraction unit for further processing and recycling ethanol to the etherification unit. A stream rich in isobutene is withdrawn from the top of the extraction unit and is fed to the isobutene purification column where isobutene is separated from higher boiling components and is withdrawn as the overhead product of the isobutene purification column. Preferably, the isobutene product stream is withdrawn in a side draw at the top of the isobutene purification column while the column is operated at total liquid reflux. Components with a lower boiling point than that of isobutene are preferably withdrawn from a top condenser of the column as off-gas. Those lighter components may comprise nitrogen or C3 hydrocarbons.

In the third embodiment of the subject of the invention, where the primary alcohol is isopropyl alcohol and the alkyl tert-butyl ether is isopropyl tert-butyl ether (IPTBE), the second distillation unit preferably comprises an isopropyl alcohol extraction unit and an isobutene purification column. The reaction mixture from the ether cleavage unit is fed to the isopropyl alcohol extraction unit where it is countercurrently contacted with a solvent, preferably with water as a solvent. A stream rich in water and isopropyl alcohol is withdrawn from the bottom of the extraction unit for further processing and recycling ethanol to the etherification unit. A stream rich in isobutene is withdrawn from the top of the extraction unit and is fed to the isobutene purification column where isobutene is separated from higher boiling components and is withdrawn as the overhead product of the isobutene purification column. Preferably, the isobutene product stream is withdrawn in a side draw at the top of the isobutene purification column while the column is operated at total liquid reflux. Components with a lower boiling point than that of isobutene are preferably withdrawn from a top condenser of the column as off-gas. Those lighter components may comprise nitrogen or C3 hydrocarbons.

In the fourth embodiment of the subject of the invention, where the primary alcohol is isobutanol and the alkyl tert-butyl ether is isobutyl tert-butyl ether (IBTBE), the second distillation unit preferably comprises a distillation column that is fed by the reaction mixture from the ether cleavage unit. Isobutene is withdrawn as the overhead product from that column, isobutanol and diisobutene being withdrawn as the bottom product and being recycled to the etherification unit. The bottom temperature is preferably from 150° C. to 200° C. and the pressure in the column is preferably from 4 to 8 bar. In a preferred variant the isobutene product stream is withdrawn in a side draw at the top of the column while the column is operated at total liquid reflux. Components with a lower boiling point than that of isobutene are preferably withdrawn from a top condenser of the column as off-gas. Those lighter components may comprise nitrogen or C3 hydrocarbons.

Advantageously, the top product contains not less than 99.3% by weight, preferably not less than 99.5% by weight, especially not less than 99.7% by weight, of isobutene. Preferably, isobutene containing not more than 500 ppm, preferably not more than 100 ppm, especially not more than 50 ppm by weight of primary alcohol is taken off as the top product.

Preferably, the high purity isobutene product is taken off from a side draw of the second distillation unit close to the top. Any water which may be created as a side product in the process can be removed from the system, e.g. in a reflux drum of a top condenser of a distillation column.

The bottom product mainly contains primary alcohol, alkyl tert-butyl ether and diisobutene. Advantageously, the bottom product contains from 80 to 85% by weight of primary alcohol, from 8 to 10% by weight of alkyl tert-butyl ether and from 4 to 5% by weight of diisobutene. The major part of the bottom product is recycled to the etherification unit. If necessary, the recycle stream may be supplemented with fresh primary alcohol.

Byproduct Separation Unit

According to the invention the plant further comprises a byproduct separation unit which is fed by a bottom purge stream of the first distillation unit and/or by a part of the bottom product of the second distillation unit. In case that a part of the bottom product of the second distillation unit is fed to the byproduct separation unit, the weight ratio of bottom product directed to the byproduct separation unit to bottom product recycled to the etherification unit is preferably in the range from 1:20 to 1:5, more preferably about 1:10.

In the byproduct separation unit this byproduct separation unit feed stream is split up in at least three byproduct streams wherein a first byproduct stream is rich in diisobutene, a second byproduct stream is rich in the primary alcohol, and a third byproduct stream is rich in components with a normal boiling point higher than 110° C.

Methanol/MTBE

In the first embodiment of the subject of the invention, where the primary alcohol is methanol and the alkyl tert-butyl ether is methyl tert-butyl ether (MTBE), the byproduct separation unit preferably comprises at least two distillation columns.

In one embodiment a first distillation column of the byproduct separation unit is fed by a bottom purge stream of the first distillation unit and/or by a part of the bottom product of the second distillation unit which mainly contains methanol, MTBE and diisobutene. A second byproduct stream rich in methanol is withdrawn from the top of the first column. This second byproduct stream may further contain MTBE. The bottom product stream of the first column is fed to the second distillation column of the byproduct separation unit. A first byproduct stream rich in diisobutene is withdrawn from the top of the second column, whereas a third byproduct stream rich in components with a normal boiling point higher than 110° C. is withdrawn from the bottom of the second column. The third byproduct stream may contain high-boiling components like triisobutene.

In another preferred embodiment the byproduct separation unit comprises at least three distillation columns. A first distillation column of the byproduct separation unit is fed by a bottom purge stream of the first distillation unit and/or by a part of the bottom product of the second distillation unit which mainly contains methanol, MTBE and diisobutene. A stream rich in MTBE is withdrawn from the top of the first column. Components with a higher normal boiling point than MTBE are withdrawn from the bottom of the first column and are fed to a second distillation column of the byproduct separation unit. A second byproduct stream rich in methanol is withdrawn from the top of the second column. The bottom product stream of the second column is withdrawn and fed to a third distillation column of the byproduct separation unit. A first byproduct stream rich in diisobutene is withdrawn from the top of the third column, and a third byproduct stream rich in components with a normal boiling point higher than 110° C. is withdrawn from the bottom of the third column. The third byproduct stream may contain high-boiling components like triisobutene.

Ethanol/ETBE

In the second embodiment of the subject of the invention, where the primary alcohol is ethanol and the alkyl tert-butyl ether is ethyl tert-butyl ether (ETBE), the byproduct separation unit preferably comprises at least two distillation columns.

In one embodiment a first distillation column of the byproduct separation unit is fed by a bottom purge stream of the first distillation unit and/or by a part of the bottom product of the second distillation unit which mainly contains ethanol, ETBE and diisobutene. A second byproduct stream rich in ethanol is withdrawn from the top of the first column.

This second byproduct stream may further contain ETBE. The bottom product stream of the first column is fed to the second distillation column of the byproduct separation unit. A first byproduct stream rich in diisobutene is withdrawn from the top of the second column, whereas a third byproduct stream rich in components with a normal boiling point higher than 110° C. is withdrawn from the bottom of the second column. The third byproduct stream may contain high-boiling components like triisobutene.

In another preferred embodiment the byproduct separation unit comprises at least three distillation columns. A first distillation column of the byproduct separation unit is fed by a bottom purge stream of the first distillation unit and/or by a part of the bottom product of the second distillation unit which mainly contains ethanol, ETBE and diisobutene. The first distillation column is a pre-fractionation column where a stream rich in ETBE and ethanol is withdrawn from the top of the column and a stream rich in diisobutene and higher boiling components is withdrawn from the bottom of the column. The top product stream is fed to a second distillation column of the byproduct separation unit where a stream rich in ETBE is withdrawn from the top of the second column, and a second byproduct stream rich in ethanol is withdrawn from the bottom of the second column. The bottom product stream of the first column is fed to a third distillation column of the byproduct separation unit where a first byproduct stream rich in diisobutene is withdrawn from the top of the third column, and a third byproduct stream rich in components with a normal boiling point higher than 110° C. is withdrawn from the bottom of the third column. The third byproduct stream may contain high-boiling components like triisobutene.

Isopropyl Alcohol/IPTBE

In the third embodiment of the subject of the invention, where the primary alcohol is isopropyl alcohol and the alkyl tert-butyl ether is isopropyl tert-butyl ether (IPTBE), the byproduct separation unit preferably comprises at least two distillation columns.

In one embodiment a first distillation column of the byproduct separation unit is fed by a bottom purge stream of the first distillation unit and/or by a part of the bottom product of the second distillation unit which mainly contains isopropyl alcohol, IPTBE and diisobutene. A second byproduct stream rich in isopropyl alcohol is withdrawn from the top of the first column. The bottom product stream of the first column is fed to the second distillation column of the byproduct separation unit. A first byproduct stream rich in diisobutene is withdrawn from the top of the second column. This first byproduct stream may further contain IPTBE. A third byproduct stream rich in components with a normal boiling point higher than 110° C. is withdrawn from the bottom of the second column. The third byproduct stream may contain high-boiling components like triisobutene.

In another preferred embodiment the byproduct separation unit comprises at least three distillation columns. A first distillation column of the byproduct separation unit is fed by a bottom purge stream of the first distillation unit and/or by a part of the bottom product of the second distillation unit which mainly contains isopropyl alcohol, IPTBE and diisobutene. The first distillation column is a pre-fractionation column where a stream rich in IPTBE and isopropyl alcohol is withdrawn from the top of the column and a stream rich in diisobutene and higher boiling components is withdrawn from the bottom of the column. The top product stream is fed to a second distillation column of the byproduct separation unit where a second byproduct stream rich in isopropyl alcohol is withdrawn from the top of the second column, and a stream rich in IPTBE is withdrawn from the bottom of the second column. The bottom product stream of the first column is fed to a third distillation column of the byproduct separation unit where a first byproduct stream rich in diisobutene is withdrawn from the top of the third column, and a third byproduct stream rich in components with a normal boiling point higher than 110° C. is withdrawn from the bottom of the third column. The third byproduct stream may contain high-boiling components like triisobutene.

Isobutanol/IBTBE

In the fourth embodiment of the subject of the invention, where the primary alcohol is isobutanol and the alkyl tert-butyl ether is isobutyl tert-butyl ether (IBTBE), the byproduct separation unit preferably comprises at least two distillation columns.

In one embodiment a first distillation column of the byproduct separation unit is fed by a bottom purge stream of the first distillation unit and/or by a part of the bottom product of the second distillation unit which mainly contains isobutanol, IBTBE and diisobutene. A first byproduct stream rich in diisobutene is withdrawn from the top of the first column. The bottom product stream of the first column is fed to the second distillation column of the byproduct separation unit. A second byproduct stream rich in isobutanol is withdrawn from the top of the second column, whereas a third byproduct stream rich in components with a normal boiling point higher than 110° C. is withdrawn from the bottom of the second column. The third byproduct stream mainly contains IBTBE and may contain further high-boiling components like diisobutyl ether (DIBE) and/or triisobutene.

In an alternative embodiment with two columns a first distillation column of the byproduct separation unit is fed by a bottom purge stream of the first distillation unit and/or by a part of the bottom product of the second distillation unit which mainly contains isobutanol, IBTBE and diisobutene. A third byproduct stream rich in components with a normal boiling point higher than 110° C. is withdrawn from the bottom of the first column. The third byproduct stream mainly contains IBTBE and may contain further high-boiling components like diisobutyl ether (DIBE) and/or triisobutene. The top product stream of the first column is fed to the second distillation column of the byproduct separation unit. A first byproduct stream rich in diisobutene is withdrawn from the top of the second column, whereas a second byproduct stream rich in isobutanol is withdrawn from the bottom of the second column.

In another alternative embodiment with two columns a first distillation column of the byproduct separation unit is fed by a bottom purge stream of the first distillation unit and/or by a part of the bottom product of the second distillation unit which mainly contains isobutanol, IBTBE and diisobutene. A third byproduct stream rich in components with a normal boiling point higher than 110° C. is withdrawn from the bottom of the first column. The third byproduct stream mainly contains IBTBE and may contain further high-boiling components like diisobutyl ether (DIBE) and/or triisobutene. A second byproduct stream rich in isobutanol is withdrawn as a side draw from the first column. The top product stream of the first column is fed to the second distillation column of the byproduct separation unit. A first byproduct stream rich in diisobutene is withdrawn from the bottom of the second column. The top product of the second column is recycled back to the first column.

More preferably, the byproduct separation unit comprises at least three distillation columns.

In one embodiment with three columns a first distillation column of the byproduct separation unit is fed by a bottom purge stream of the first distillation unit and/or by a part of the bottom product of the second distillation unit which mainly contains isobutanol, IBTBE and diisobutene. A third byproduct stream rich in components with a normal boiling point higher than 110° C. is withdrawn from the bottom of the first column. The third byproduct stream mainly contains high boiling components like triisobutene. The top product stream of the first column is fed to a second distillation column. A second byproduct stream rich in isobutanol is withdrawn from the bottom of the second column. The top product stream of the second column is fed to a third distillation column where a first byproduct stream rich in diisobutene is withdrawn from the bottom of the column. The first byproduct stream may also contain IBTBE and/or diisobutyl ether (DIBE).

In a preferred embodiment the second byproduct stream rich in the primary alcohol is recycled to the etherification unit. The recycle of the primary alcohol increases the overall efficiency of the isobutene separation process by reducing the amount of fresh primary alcohol needed for the isobutene separation. In processes according to the prior art, the amount of primary alcohol contained in the purge stream taken from the second distillation unit is typically discharged.

In a further preferred embodiment the mass fraction of the primary alcohol in the second byproduct stream is at least 90 wt.-%, preferably at least 95 wt.-%. When the second byproduct stream is recycled to the etherification unit, the high purity of the primary alcohol increases the overall efficiency of the isobutene separation process by reducing the amount of fresh primary alcohol needed for the isobutene separation.

In a preferred embodiment the first byproduct stream is further split up in at least two further byproduct streams wherein a fourth byproduct stream is rich in diisobutene and a fifth byproduct stream is rich in alkyl tert-butyl ether. The provision of a further separation of the first byproduct stream increases the flexibility of the isobutene separation process, e.g. in terms of process integration by recycling streams to dedicated process units. Furthermore, the overall efficiency of the process is increased.

For a process where the first byproduct stream is further split up in at least two further byproduct streams, it is preferred that the mass fraction of diisobutene in the first byproduct stream is at least 30 wt.-% and the mass fraction of diisobutene in the fourth byproduct stream is at least 90 wt.-%, more preferably at least 95 wt.-%, most preferably at least 98 wt.-%, in particular at least 99 wt.-%. The provision of a byproduct stream with a high to very high purity of diisobutene enables the use of that component in various applications and thus increases the overall efficiency of the isobutene separation process.

For a process where the first byproduct stream is further split up in at least two further byproduct streams, it is preferred that the fifth byproduct stream is at least partly recycled to the evaporator for evaporation and/or to the ether cleavage unit. By recycling the fifth product stream rich in alkyl tert-butyl ether the loss of the valuable product isobutene contained in the alkyl tert-butyl ether is reduced. This increases the overall efficiency of the isobutene separation process.

The invention is explained in more detail below with reference to the drawings. The drawings are to be interpreted as in-principle presentation. They do not constitute any restriction of the invention, for example with regards to specific embodiments. In the figures:

LIST OF REFERENCE NUMERALS USED

Figure 1:
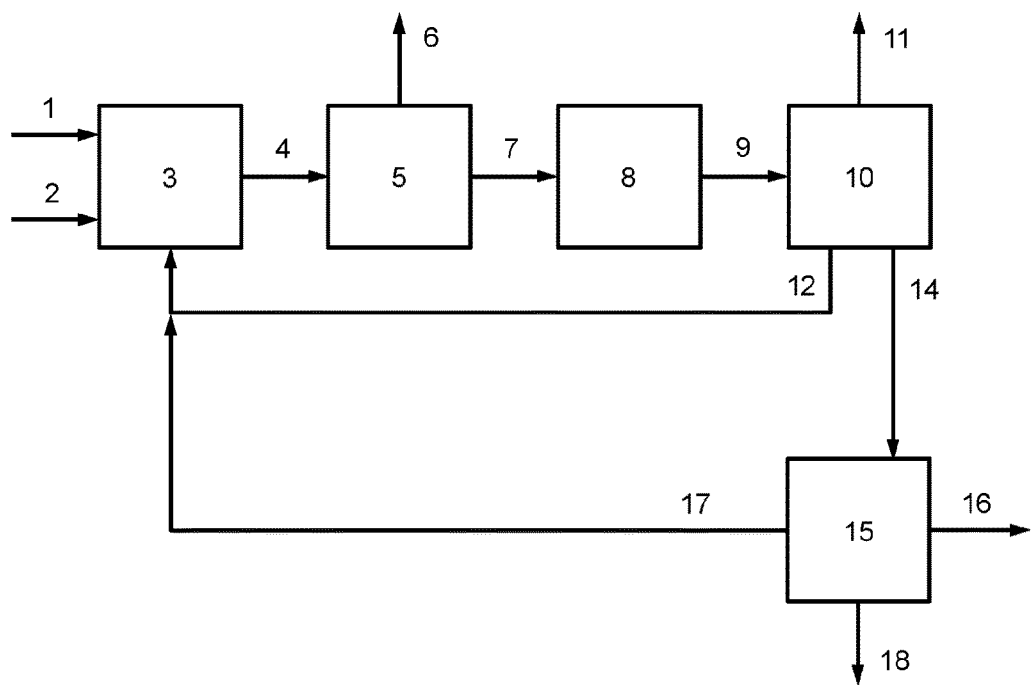
FIG. 1 shows a block diagram of a first embodiment of the process according to the invention.

1 . . . C4-hydrocarbon feed stream
2 . . . primary alcohol feed stream
3 . . . etherification unit
4 . . . reaction mixture stream
5 . . . first distillation unit
6 . . . C4-hydrocarbon raffinate stream
7 . . . alkyl tert-butyl ether bottom stream
8 . . . ether cleavage unit
9 . . . reaction mixture stream
10 . . . second distillation unit
11 . . . isobutene product stream
12 . . . primary alcohol recycle stream
13 . . . bottom purge stream
14 . . . byproduct separation unit feed stream
15 . . . byproduct separation unit
16 . . . first byproduct stream
17 . . . second byproduct stream
18 . . . third byproduct stream
19 . . . fourth byproduct stream
20 . . . fifth byproduct stream FIG. 1 shows a block diagram of a first embodiment of the process for obtaining isobutene from an isobutene containing C4-hydrocarbon mixture according to the invention. An isobutene containing C4-hydrocarbon feed stream 1 and a primary alcohol feed stream 2 are fed to an etherification unit 3 which comprises at least one reactor with an acidic catalyst, preferably an ion exchange resin. Advantageously, the etherification unit 3 comprises a fixed bed reactor, e.g. a flow tube or a loop reactor or a combination of both types. The C4-hydrocarbon mixture is contacted with the primary alcohol, the mixture reacting in the presence of the acid catalyst to form the corresponding alkyl tert-butyl ether as an intermediate product and diisobutene as a by-product.

The reaction mixture 4 obtained is fed to a first distillation unit 5. A C4-hydrocarbon raffinate stream 6 is withdrawn as the overhead product of the first distillation unit 5. The bottom product stream 7 withdrawn from the first distillation unit 5 comprises mainly alkyl tert-butyl ether and diisobutene. Excess primary alcohol and heavy components, typically with a normal boiling point of more than 110° C., may be present in the bottom product stream 7 as well. The bottom product stream 7 is withdrawn as a liquid or a vaporous stream. In case that it is withdrawn as a liquid stream, it is vaporized in an evaporator.

The vaporous alkyl tert-butyl ether bottom stream 7 is fed to an ether cleavage unit 8 which comprises at least one reactor with an acidic catalyst, preferably an ion exchange resin. Advantageously, the at least one reactor in the ether cleavage unit 8 is a fixed bed reactor. Isobutene and the primary alcohol are obtained as reaction products.

The reaction mixture 9 obtained is fed to a second distillation unit 10. A highly pure isobutene product stream 11 is withdrawn as the overhead product of the second distillation unit 10. The bottom product withdrawn from the second distillation unit 10 comprises mainly primary alcohol and diisobutene. Heavy components, typically with a normal boiling point of more than 110° C., may be present in the bottom product as well. The main portion of the bottom product of the second distillation unit 10 is recycled to the etherification unit 3 in a primary alcohol recycle stream 12. If necessary, the recycle stream may be supplemented with fresh primary alcohol.

The remaining smaller portion of the bottom product of the second distillation unit 10 is fed to a byproduct separation unit 15. In this unit the byproduct separation unit feed stream 14 is split up in at least three byproduct streams, preferably in three interconnected distillation columns. A first byproduct stream 16 is rich in diisobutene and is removed from the plant. A second byproduct stream 17 is rich in the primary alcohol and is recycled to the etherification unit 3. A third byproduct stream 18 is rich in components with a normal boiling point higher than 110° C. and is removed from the plant as well.

Figure 2:
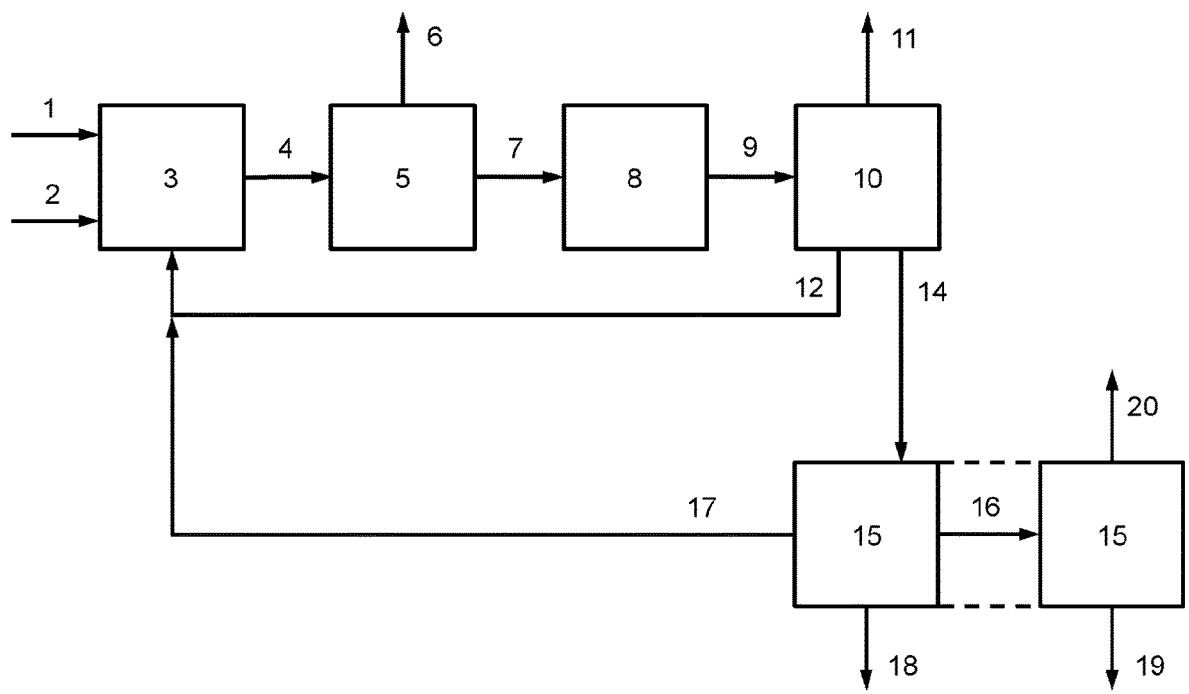
FIG. 2 shows a block diagram of a second embodiment of the process according to the invention.

FIG. 2 shows a block diagram of a second embodiment of the process for obtaining isobutene from an isobutene containing C4-hydrocarbon mixture according to the invention. In this embodiment, the first byproduct stream 16 is further split up in at least two further byproduct streams wherein a fourth byproduct stream 19 is rich in diisobutene and a fifth byproduct stream 20 is rich in alkyl tert-butyl ether.

Figure 3:
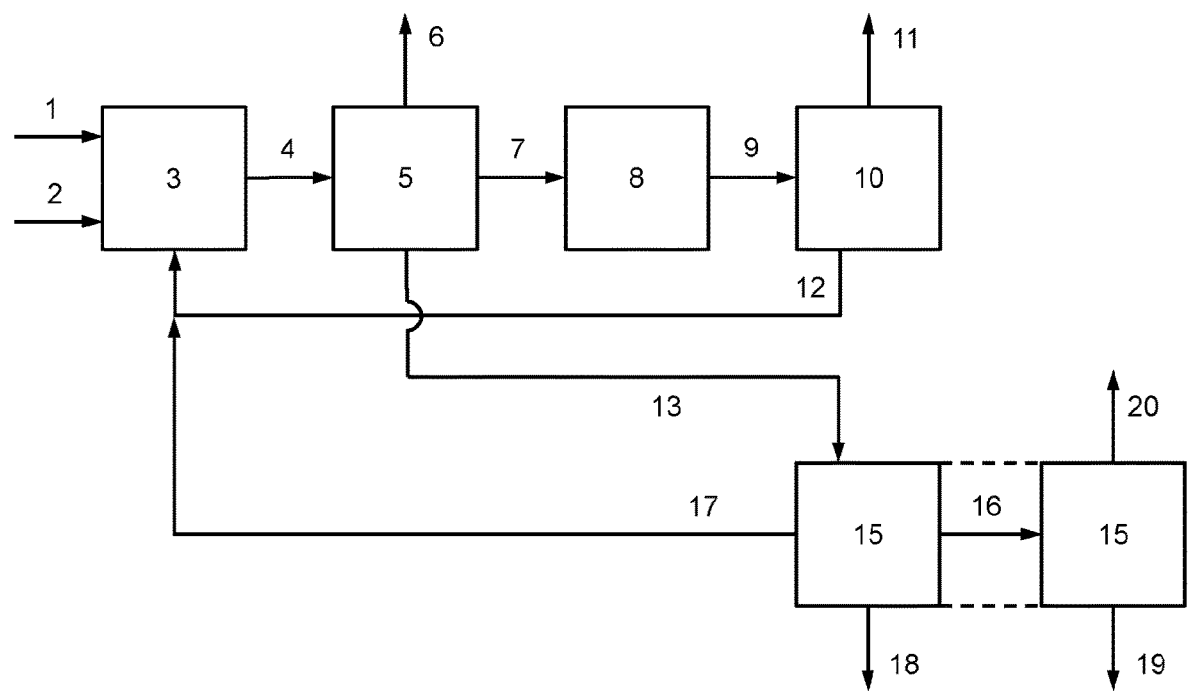
FIG. 3 shows a block diagram of a third embodiment of the process according to the invention.

FIG. 3 shows a block diagram of a third embodiment of the process for obtaining isobutene from an isobutene containing C4-hydrocarbon mixture according to the invention. In this embodiment, the bottom product of the second distillation unit 10 is completely recycled to the etherification unit 3 in a primary alcohol recycle stream 12. If necessary, the recycle stream may be supplemented with fresh primary alcohol. The byproduct separation unit 15 is fed by a bottom purge stream 13 rich in high-boiling components from the first distillation unit 5. The first byproduct stream 16 is further split up in at least two further byproduct streams wherein a fourth byproduct stream 19 is rich in diisobutene and a fifth byproduct stream 20 is rich in alkyl tert-butyl ether.

Figure 4:
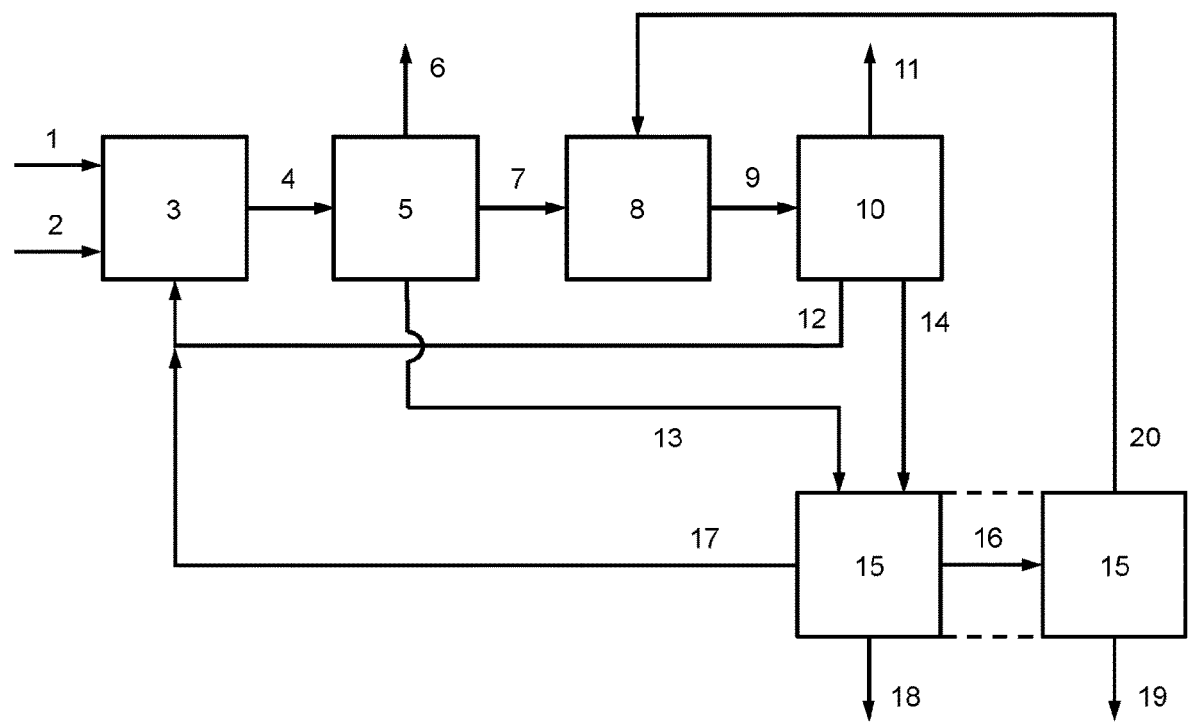
FIG. 4 shows a block diagram of a fourth embodiment of the process according to the invention.

FIG. 4 shows a block diagram of a fourth embodiment of the process for obtaining isobutene from an isobutene containing C4-hydrocarbon mixture according to the invention. In this embodiment, the first byproduct stream 16 is further split up in at least two further byproduct streams wherein a fourth byproduct stream 19 is rich in diisobutene and a fifth byproduct stream 20 is rich in alkyl tert-butyl ether. The fifth byproduct stream 20 is at least partly recycled to the ether cleavage unit 8. The first distillation unit 5 comprises a distillation column, the bottom product 7 being withdrawn as a side stream from the distillation column at a stage below the feed stage, and a bottom purge stream 13 rich in high-boiling components being withdrawn from the sump of the distillation column. The bottom purge stream 13 from the sump of the distillation column in the first distillation unit 5 is fed to the byproduct separation unit 15.

Example 1

A process for obtaining isobutene from an isobutene containing C4-hydrocarbon mixture was performed in a plant comprising an etherification unit 3, a first distillation unit 5, an ether cleavage unit 8, a second distillation unit 10 and a byproduct separation unit 15 according to the block diagram shown in FIG. 1.

The C4-hydrocarbon mixture 1 contained 5.9 wt.-% isobutane, 14.0 wt,-% n-butane, 40.2 wt.-% isobutene, 27.6 wt.-% 1-butene, 7.3 wt.-% trans-2-butene and 5.0 wt.-% cis-2-butene and was fed to the etherification unit at a flow rate of 17588.5 kg/h.

Isobutanol was supplied to the etherification unit in a stream that contained 83.0 wt.-% isobutanol, 8.3 wt.-% isobutyl tert-butyl ether (IBTBE), 4.3 wt.-% diisobutyl ether (DIBE), 3.9 wt.-% diisobutene (DIB), 0.4 wt.-% triisobutene (TIB) and traces of isobutene, tert-butanol and water at a flow rate of 13999.6 kg/h.

The etherification unit 3 comprised three fixed bed reactors with an ion exchange resin as acidic catalyst connected in series. The C4-hydrocarbon mixture was contacted with isobutanol and reacted in the presence of the acidic catalyst to form isobutyl tert-butyl ether (IBTBE) as an intermediate product and DIB as a by-product. The weight fraction of IBTBE was 53.5 wt.-% and that of DIB 1.9 wt.-%. Besides the non-reactive components of the C4-hydrocarbon mixture the reaction mixture contained 2 wt.-% DIBE, 0.2 wt.-% TIB and 8.5 wt.-% unreacted isobutanol.

The reaction mixture 4 obtained was fed to a first distillation unit 5 where a C4-hydrocarbon raffinate stream 6 was withdrawn as the overhead product of the first distillation unit 5. The bottom product stream 7 withdrawn from the first distillation unit 5 comprised 80.9 wt.-% IBTBE and 2.8 wt.-% DIB. The bottom product stream 7 further contained 12.8 wt.-% unreacted excess isobutanol and heavy components with a normal boiling point of more than 110° C., in particular 3 wt.-% DIBE and 0.3 wt.-% TIB. The bottom product was withdrawn as a liquid stream and was vaporized in an evaporator.

The vaporous bottom product stream 7 from the first distillation unit 5 was fed to an ether cleavage unit 8 which comprised two fixed bed reactors with an ion exchange resin as acidic catalyst connected in series. The reaction product comprised 32.6 wt.-% isobutene, 55.6 wt.-% isobutanol, 5.4 wt.-% IBTBE, 3 wt.-% DIBE, 2.8 wt.-% DIB and 0.3 wt.-% TIB.

The reaction mixture 9 obtained was fed to a second distillation unit 10. A highly pure isobutene product stream 11 was withdrawn as the overhead product of the second distillation unit 10. The bottom product withdrawn from the second distillation unit 10 comprised mainly isobutanol with smaller amounts of IBTBE, DIBE, DIB and TIB.

The main portion of the bottom product of the second distillation unit 10 was recycled to the etherification unit 3 in a primary alcohol recycle stream 12. The recycle stream was supplemented with fresh isobutanol. The remaining smaller portion of the bottom product of the second distillation unit 10 was fed to a byproduct separation unit 15. The weight ratio of bottom product directed to the byproduct separation unit to bottom product recycled to the etherification unit was 1:9.1 The byproduct separation unit comprised two distillation columns. The bottom product from the second distillation unit was fed to the first column of the byproduct separation unit at a feed flow rate of 1380 kg/h. The composition of the feed stream is given in Table 1 below in weight fractions. The first column was equipped with structured packings corresponding to 18 theoretical stages and was operated under a top pressure of 1 bar (abs) and a temperature at the top of 101° C. The bottom temperature was 108° C. The feed was introduced into the column in the middle of the structured packings at theoretical stage 9. A first byproduct stream 16 rich in diisobutene was withdrawn from the top of the first column at a flow rate of 144.6 kg/h and was removed from the plant. The composition of the first byproduct stream is given in Table 1. The weight fraction of DIB in the first byproduct stream was 27.6 wt.-% which corresponded to 68.8 wt.-% of the total DIB fed to the byproduct separation unit.

contained valuable isobutanol, was recycled to the etherification unit. Thus, the separation of the withdrawn part of the bottom product of the second distillation unit into three different fractions enabled a higher process integration and a reduction of operating costs. The valuable by-product diisobutene was easily recovered in contrast to known processes where it is discharged.

TABLE 1

| byproduct | | first byproduct stream (144.6 kg/h) | | second byproduct stream (1206.4 kg/h) | | third byproduct stream (24.3 kg/h) | |
|---|---|---|---|---|---|---|---|
| | feed wt. % | wt.-% | wt.-% of Feed | wt.-% | wt.-% of Feed | wt.-% | wt.-% of Feed |
| Isobuten | 0.04 | 0.23 | 54.31 | 0.00 | 0.00 | 0.00 | 0.00 |
| DIB | 4.20 | 27.61 | 68.80 | 1.47 | 30.58 | 0.08 | 0.03 |
| Isobutanol | 82.68 | 40.37 | 5.11 | 88.09 | 93.14 | 70.11 | 1.49 |
| IBTBE | 8.10 | 22.78 | 29.45 | 6.44 | 69.53 | 1.31 | 0.28 |
| DIBE | 4.48 | 9.02 | 21.08 | 3.99 | 77.89 | 0.96 | 0.38 |
| TIB | 0.49 | 0.00 | 0.00 | 0.00 | 0.36 | 27.54 | 99.63 |

The bottom product stream of the first column was fed to the second distillation column of the byproduct separation unit. The second column was equipped with random packings corresponding to 6 theoretical stages and was operated under a top pressure of 1 bar (abs) and a temperature at the top of 109° C. The bottom temperature was 115° C. The feed was introduced into the column in the lowermost packing section. A second byproduct stream 17 rich in isobutanol was withdrawn from the top of the second column at a flow rate of 1206.4 kg/h and was recycled to the etherification unit 3. The composition of the second byproduct stream is given in Table 1. The weight fraction of isobutanol in the second byproduct stream was 88.1 wt.-% which corresponded to 93.1 wt.-% of the total isobutanol fed to the byproduct separation unit.

A third byproduct stream 18 rich in components with a normal boiling point higher than 110° C. was withdrawn from the bottom of the second column at a flow rate of 24.3 kg/h and was removed from the plant. The composition of the third byproduct stream is given in Table 1. The weight fraction of triisobutene (normal boiling point of 177° C.) in the third byproduct stream was 27.6 wt.-% which corresponded to 99.6 wt.-% of the total TIB fed to the byproduct separation unit.

In comparison with a conventional plant without a byproduct separation unit, the provision of a byproduct separation unit that is fed by a part of the bottom product of the second distillation unit significantly increased the operational window of the plant. In a process according to the invention as well as in a conventional process it is necessary to remove high boiling impurities to avoid an accumulation of these substances in apparatus of the process where they would lead to malfunction or even a shutdown of the process. In contrast to the conventional process where valuable products are lost along with the removal of the impurities, the process according to the invention enabled the continuous removal of high boiling impurities from the system with simultaneous recycling or further use of valuable products like isobutanol and DIB. In the example shown only 24.3 kg/h of the bottom product stream withdrawn from the second distillation unit of 1380 kg/h was removed from the process as high boiling impurities. The major part of the bottom product stream, which mainly Example 2

As a further example, simulation results are presented for a byproduct separation unit with three distillation columns. The simulations were carried out in the inhouse simulation tool "Chemasim". The simulation tool is equation-based and uses physical property data by AspenTech (20 Crosby Drive, Bedford, MA 01730, U.S.A., www.aspentech.com). A non-random two-liquid (NRTL) model was used to calculate the vapor-liquid-equilibria.

In the simulation, a portion of the bottom product of the second distillation unit 10 was fed to stage 4 (counted from bottom to top) of a first distillation column of the byproduct separation unit 15 at a feed flow rate of 1248.5 kg/h. The composition of the feed stream is given in Table 2 below in weight fractions. The first column contained 7 theoretical stages and was operated under a top pressure of 1.8 bar (abs) and a temperature at the top of 122° C. The bottom temperature was 150° C. A third byproduct stream 18 rich in components with a normal boiling point higher than 110° C. was withdrawn from the bottom of the first column at a flow rate of 18.2 kg/h and was removed from the plant. The composition of the third byproduct stream is given in Table 1. The weight fraction of triisobutene (normal boiling point of 177° C.) in the third byproduct stream was 71.9 wt.-% which corresponded to 99.9 wt.-% of the total TIB fed to the byproduct separation unit.

The top product stream of the first column was fed to stage 8 (counted from bottom to top) of the second distillation column of the byproduct separation unit. The second column contained 16 theoretical stages and was operated under a top pressure of 0.3 bar (abs) and a temperature at the top of 69° C. The bottom temperature was 75° C. A second byproduct stream 17 rich in isobutanol was withdrawn from the bottom of the second column at a flow rate of 976.6 kg/h and was recycled to the etherification unit 3. The composition of the second byproduct stream is given in Table 1. The weight fraction of isobutanol in the second byproduct stream was 95.0 wt.-% which corresponded to 99.2 wt.-% of the total isobutanol fed to the byproduct separation unit.

The top product stream of the second column was fed to stage 12 (counted from bottom to top) of the third distillation column of the byproduct separation unit. The third column contained 17 theoretical stages and was operated under a top pressure of 5 bar (abs) and a temperature at the top of 152°

C. The bottom temperature was 182° C. A first byproduct stream 16 rich in diisobutene was withdrawn from the bottom of the first column at a flow rate of 243.6 kg/h and was removed from the plant. The composition of the first byproduct stream is given in Table 1. The weight fraction of DIB in the first byproduct stream was 28.8 wt.-% which corresponded to 89.5 wt.-% of the total DIB fed to the byproduct separation unit.

In comparison with Example 1 the efficiency of the separation of the byproduct feed stream into valuable byproduct stream could be further increased. In the example shown only 18.2 kg/h of the bottom product stream withdrawn from the second distillation unit of 1248.5 kg/h was removed from the process as high boiling impurities.

TABLE 2

| byproduct | feed wt. % | first byproduct stream (243.6 kg/h) | | second byproduct stream (976.6 kg/h) | | third byproduct stream (18.2 kg/h) | |
|---|---|---|---|---|---|---|---|
| | | wt.-% | wt.-% of Feed | wt.-% | wt.-% of Feed | wt.-% | wt.-% of Feed |
| Isobuten | 0.10 | 0.00 | 0.00 | 0.00 | 0.00 | 0.00 | 0.00 |
| DIB | 6.29 | 28.85 | 89.49 | 0.50 | 6.22 | 0.03 | 0.01 |
| Isobutanol | 74.91 | 0.05 | 0.01 | 94.96 | 99.16 | 26.85 | 0.52 |
| IBTBE | 10.43 | 43.43 | 81.26 | 2.30 | 17.22 | 0.59 | 0.08 |
| DIBE | 7.22 | 27.68 | 74.77 | 2.25 | 24.33 | 0.59 | 0.12 |
| TIB | 1.05 | 0.00 | 0.00 | 0.00 | 0.09 | 71.94 | 99.92 |

The invention claimed is:

1. A process for obtaining isobutene from an isobutene containing C4-hydrocarbon mixture in a plant comprising an etherification unit, a first distillation unit, an ether cleavage unit and a second distillation unit, the process comprising:
    (a) contacting the C4-hydrocarbon mixture with a primary alcohol and reacting the C4-hydrocarbon mixture with the primary alcohol in the presence of an acidic catalyst to form a corresponding alkyl tert-butyl ether as an intermediate product as an effluent and diisobutene as a by-product in the etherification unit;
    (b) distilling the effluent from the etherification unit in the first distillation unit, a C4-hydrocarbon raffinate being withdrawn as the overhead product, the alkyl tert-butyl ether and diisobutene being withdrawn as a liquid or vaporous bottom product, and vaporizing the bottom product if the bottom product is withdrawn as a liquid forming vaporous bottom product;
    (c) reacting the vaporous bottom product in the presence of an acidic catalyst obtaining isobutene and the primary alcohol as reaction products in the ether cleavage unit;
    (d) distilling the reaction products from the ether cleavage unit in the second distillation unit, isobutene being withdrawn as the overhead product, the primary alcohol and diisobutene being withdrawn as the bottom product and being recycled to the etherification unit;
    characterized in that the plant further comprises a byproduct separation unit being fed by a feed stream comprising a bottom purge stream of the first distillation unit and/or by a part of the bottom product of the second distillation unit, this feed stream being split up in at least three byproduct streams wherein a first byproduct stream is rich in diisobutene, a second byproduct stream is rich in the primary alcohol, and a third byproduct stream is rich in components with a normal boiling point higher than 110° C.

2. The process according to claim 1, wherein the second byproduct stream is recycled to the etherification unit.

3. The process according to claim 1, wherein the mass fraction of the primary alcohol in the second byproduct stream is at least 90 wt.-%.

4. The process according to claim 1, wherein the first byproduct stream is further split up in at least two further byproduct streams wherein a fourth byproduct stream is rich in diisobutene and a fifth byproduct stream is rich in alkyl tert-butyl ether.

5. The process according to claim 4, wherein the mass fraction of diisobutene in the first byproduct stream is at least 30 wt.-% and the mass fraction of diisobutene in the fourth byproduct stream is at least 90 wt.-%.

6. The process according to claim 4, wherein the fifth byproduct stream is at least partly recycled to the evaporator for evaporation and/or to the ether cleavage unit.

7. The process according to claim 1, wherein the first distillation unit comprises a distillation column, the bottom product being withdrawn as a side stream from the distillation column at a stage below the feed stage, and a bottom purge stream rich in high-boiling components being withdrawn from the sump of the distillation column.

8. The process according to claim 7, wherein the bottom purge stream from the sump of the distillation column in the first distillation unit is fed to the byproduct separation unit.

9. The process according to claim 1, wherein the bottom product from the first distillation unit is vaporized in an evaporator, a bottom purge stream containing high boiling components with a normal boiling point higher than that of the alkyl tert-butyl ether being withdrawn from the evaporator.

10. The process according to claim 9, wherein the evaporator is a natural circulation evaporator, particularly a Robert type evaporator, and wherein the bottom purge stream is withdrawn from the liquid phase in the bottom of the evaporator.

11. The process according to claim 9, wherein the bottom purge stream from the evaporator is fed to the byproduct separation unit.

12. The process according to claim 1, wherein the primary alcohol is isobutanol, and the alkyl tert-butyl ether is isobutyl tert-butyl ether (IBTBE).

* * * * *